(12) United States Patent
Soldin

(10) Patent No.: US 8,227,259 B2
(45) Date of Patent: *Jul. 24, 2012

(54) FREE THYROXINE AND FREE TRIIODOTHYRONINE ANALYSIS BY MASS SPECTROMETRY

(75) Inventor: Steven J. Soldin, Bethesda, MD (US)

(73) Assignee: Georgetown University, Washington, DC (US)

( * ) Notice: Subject to any disclaimer, the term of this patent is extended or adjusted under 35 U.S.C. 154(b) by 1027 days.

This patent is subject to a terminal disclaimer.

(21) Appl. No.: 11/253,670

(22) Filed: Oct. 20, 2005

(65) Prior Publication Data

US 2006/0223188 A1 Oct. 5, 2006

Related U.S. Application Data

(60) Provisional application No. 60/666,712, filed on Mar. 31, 2005.

(51) Int. Cl.
*G01N 33/53* (2006.01)
(52) U.S. Cl. .................... 436/500; 436/161; 436/173
(58) Field of Classification Search .............. 436/86, 436/169, 171, 500, 161, 173
See application file for complete search history.

(56) References Cited

U.S. PATENT DOCUMENTS

| | | |
|---|---|---|
| 4,741,897 A | 5/1988 | Andrews |
| 2004/0235188 A1 | 11/2004 | Soldin |

FOREIGN PATENT DOCUMENTS

| | | |
|---|---|---|
| WO | 0188548 | 11/2001 |
| WO | 0246772 | 6/2002 |

OTHER PUBLICATIONS

Isotope Dilution-Liquid Chromatography/Electrospray Ionization-Tandem Mass Spectrometry for the Determination of Serum Thyroxine as a Potential Reference Method Veronique I. De Brabandere, Pin Hou, Dietmar Stockl, Linda M. Thienpont, Andre P. Leenheer Rapid Communications in Mass Spectrometry 12, 1099-1103 (1998).*
Ultrafiltration Devices Tested for use in a Free Thyroxine Assay Validated by Comparison with Equilibrium Dialysis S. Tikanoja Scandinavian Journal of Clinical and Laboratory Investigation 1990; 50: 663-669.*
Measurements of Serum-Free Thyroid Hormone Concentrations by Ultrafiltration—a Comparision with Equilibrium Dialysis and Mathematical Calculation Norimichi Konno, Kohji Hagiwara, Hideo Taguchi, Shigeki Murkami, Shizuko Taguchi Annals of Nuclear Medicine vol. 1, No. 1, 15-22 (1987).*

(Continued)

*Primary Examiner* — Robert J Hill, Jr.
*Assistant Examiner* — Dwan A Gerido
(74) *Attorney, Agent, or Firm* — McCarter & English, LLP; Danielle L. Herritt, Esq.

(57) ABSTRACT

Methods, systems and kits for the simultaneous or sequential analysis of one or more hormones by mass spectrometry are disclosed. The methods require minimal sample size and minimal preparation time. The methods comprise ionizing the hormones and analyzing the hormones by mass spectrometry. In addition, methods, systems and kits for the simultaneous or sequential analysis of free thyroxine (FT4) hormone and free-triiodothyronine (FT3) is disclosed comprising ionization of the FT4 and FT3 hormone in the negative mode using an electrospray source.

32 Claims, 12 Drawing Sheets

OTHER PUBLICATIONS

New Ultrafiltration Method for Free thyroxin Compared with Equilibrium Dialysis in Patients with Thyroid Dysfunction and Non thyroidal Illness. Sari Tikanoja and B. Kristian Liewendahl Clinical Chemistry 36/5, 800-804 (1990).*

Soukhova, N. et al. "Isotope Dilution Tandem Mass Spectrometric Method for T4/T3" Clinica Chimica Acta, Elsevier BV, Amsterdam, NL, vol. 343, No. 1/02, Jan. 1, 2004, pp. 185-190.

Gu et al. Simultaneous quantification of free triiodothryonine and free thyroxine by isotope dilution tandem mass spectrometry:, Dec. 2007, Clinical Biochemisty, vol. 40, NR. 18, pp. 1386-1391.

European Search Report for EP 05 85 1243 dated Mar. 11, 2009.

Siekmann, L., "Measurement of thyroxine in human serum by isotope dilution mass spectrometry. Definitive methods in clinical chemistry, V", Biomedical and Environmental Mass Spectrometry, vol. 14, No. 11, Nov. 1987, pp. 683-688.

Thienpont, L.M. et al., "Development of a new method for the determination of thyroxine in serum based on isotope dilution gas chromatography mass spectrometry", Biol Mass Spectrom, vol. 23, No. 8, 1994, pp. 475-482.

De Brabandere, Vi et al., "Isotope dilution-liquid chromatography/ electrospray ioniztion-tandem mass spectrometry for the determination of serum thyroxine as a potential reference method", Rapid Commun Mass Spectrom, vol. 12, No. 16, 1998, pp. 1099-1103.

Kosaka, Takeo et al., "Analysis of thyroid hormones in health foods by LC/MS" Shokuhin Elseigaku Zasshi, vol. 43, No. 4, Aug. 2002, pp. 225-229.

Tai, SSC et al., "Candidate reference method for total thyroxine in human serum: use of isotope dilution liquid chromatography-mass spectometry with electrospray ionization", Clinical Chemistry, vol. 48, No. 4, 2002, pp. 637-642.

Chang, Y-C et al., "Quantitative measurement of male steroid hormones using automated on line solid phase extraction liquid chromotography tandem mass spectrometry and comparison with radioimmunoassay", Analyst, vol. 128, No. 4, Apr. 1, 2003, pp. 363-368.

International Search Report for PCT/CA2004/000555, dated Jul. 22, 2004.

Thienpont, Linda M. et al., Isotope Dilution-Gas Chromatography/ Mass Spectrometry and Liquid Chromotography/Electrospray Ionization-Tandem Mass Spectrometry for the Determination of Triiodo-L-Thyronine in Serum, 1999, Rapid Communications in Mass Spectroscopy, 13, 1924-1931.

Kissmeyer, Anne Marie et al., Determination of the vitamin D analog EP 1089 (seocalcitol) in human and pig serum using liquid chromatography-tandem mass spectrometry, 2000, Journal of Chromatography B, 740, 117-128.

Jonsson, Bo A.G., et al., Determination of cotrisol in human saliva using liquid chromatography-electrospray tandem mass spectrometry, 2003, Journal of Chromatography B, 784, 63-68.

International Search Report for PCT/US 05/382232 dated Sep. 13, 2007.

Leinonen, Antti, et al., Liquid chromatography/mass spectrometry in anabolic steroid analysis—optimization and comparison of three ionization techniques: electrospray ionization, atmospheric pressure chemical ionization and atmospheric pressure photoionization, 2002, Journal Mass Spectrometry, 37, 693-698.

Fredline, Victoria F. et al., A Reference Method for the Analysis of Aldosterone in Blood by High-Performance Liquid Chromatography-Atmospheric Pressure Chemical Ionization—Tandem Mass Spectrometry, 1997, Analytical Biochemistry, 252, 308-313.

Vogeser, Michael et al., Determination of Serum Cortisol by Isotope-Dilution Liquid-Chromatography Electospray Ionization Tandem Mass Spectrometry with On-line Extraction, 2001 Clin Chem Lab, 39(10), 944-947.

Draisci, R. et al., Quantitation of anabolic hormones and their metabolism in bovine serum and urine by liquid chromatography-tandem mass spectrometry, 2000, Journal of Chromatography A., 870, 511-522.

Notice of Allowance for U.S. Appl. No. 10/823,690 dated Jul. 10, 2009.

Office action summary for U.S. Appl. No. 10/823,690 dated Sep. 15, 2008.

Office action summary for U.S. Appl. No. 10/823,690 dated Jan. 22, 2008.

Office action summary for U.S. Appl. No. 10/823,690 dated Jul. 27, 2007.

European office action for application 04727197.8 dated Dec. 12, 2008.

International Preliminary Report on Patentability dated Oct. 14, 2005 and Written Opinion for International Application No. PCT/CA2004/ 000555.

European office action for 05851243.5 dated Apr. 1, 2009.

European office action 05851243.5 dated Aug. 3, 2009.

Communication pursuant to Article 94(3) EPC from the European Patent Office for application No. 05851243.5 dated Jul. 2, 2010.

Clark, William et al. "Analysis of free hormone fractions by an ultrafast immunoextraction/displacement immunoassay: studies using free thyroxine as a model system." Analytical Chemistry, vol. 77, No. 6, pp. 1859-1866. Mar. 15, 2005 (published on the Internet Feb. 11, 2005).

* cited by examiner

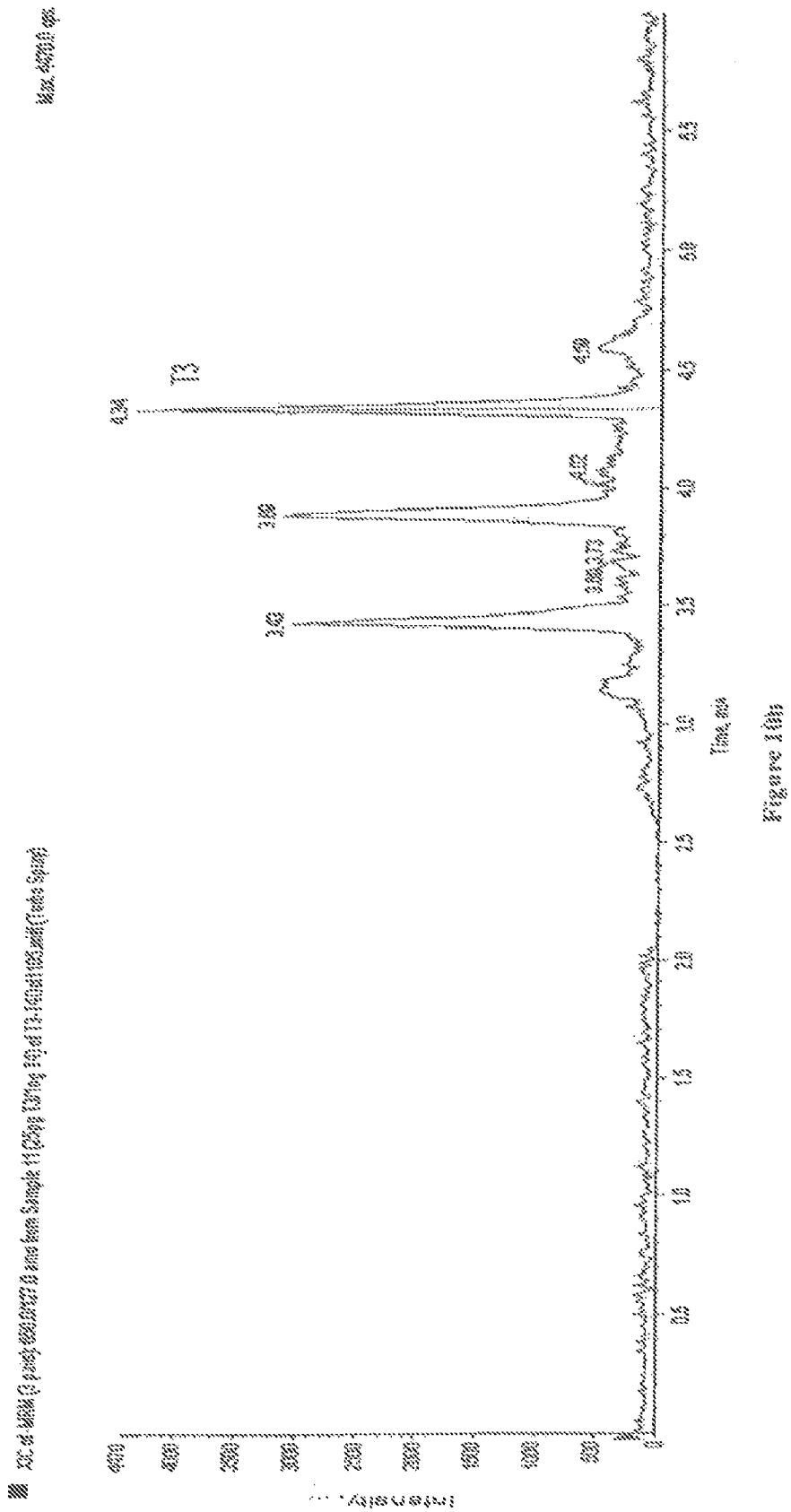

FREE THYROXINE AND FREE TRIIODOTHYRONINE ANALYSIS BY MASS SPECTROMETRY

CROSS REFERENCE TO OTHER APPLICATIONS

This application claims priority to U.S. provisional application 60/666,712 filed Mar.31, 2005.

FIELD

The invention relates to methods and kits for analyzing free thyroxine (FT4) and free triiodothyronine (FT3) thyroid hormones by mass spectrometry.

BACKGROUND

Hormones are biological messengers. They are synthesized by specific tissues (glands) and are secreted into the blood. The blood carries them to target cells where they act to alter the activities of the target cells.

Hormones are chemically diverse, and are generally categorized into three main groups: (1) small molecules derived from amino acids, for example thyroxine, (2) polypeptides or proteins, for example insulin and thyroid-stimulating hormone, and (3) molecules derived from cholesterol, for example steroids.

An important class of hormone is the thyroid hormones. Examples of thyroid hormones are thyroxine (T4), free thyroxine (FT4), triiodothyronine (T3) and free triiodothyronine (FT3). T4 and T3 enter cells and bind to intracellular receptors where they increase the metabolic capabilities of the cell by increasing mitochondria and mitochondrial enzymes. T4 and T3 are important in regulating a number of biological processes, including growth and development, carbohydrate metabolism, oxygen consumption, protein synthesis and fetal neurodevelopment. Synthesis of all circulating T4 and a small percentage of circulating T3 occurs on thyroglobulin molecules located within the thyroid. The bulk of the T3 present in the blood is produced enzymatically via monodeiodination of T4 by specific intracellular deiodinases—enzymes present in the follicular cells and the cells of target tissues [1]. In serum drawn from healthy human subjects, total T4 is present at about 60-fold higher concentration than total T3. T4 acts as a prohormone, as the reservoir for the production of T3, the active hormone. The metabolic activity associated with thyroid hormone (TH) is initiated by T3 binding to specific nuclear receptors within target cells. Thyroid hormone concentrations in blood are essential tests for the assessment of thyroid function.

Steroids make up another important class of hormones. Examples of steroid hormones include estrogens, progesterone and testosterone. Estrogen is the name of a group of hormones of which there are three principle forms, estrone, estradiol and estriol. Estrogens and progesterone cause the development of the female secondary sexual characteristics and develop and maintain the reproductive function. Testosterone develops and maintains the male secondary sex characteristics, promotes growth and formation of sperm. Steroids enter target cells and bind to intracellular receptors and then cause the production of mRNA coding for proteins that manifest the changes induced by steroids.

The accurate analysis and quantification of hormones is becoming more important. For example, estrogen and estrogen-like compounds are playing an ever-increasing role in today's society through hormone replacement therapy. Also, the analysis and quantification of estrogen and estrogen-like compounds helps in the management of estrogen-related diseases, like breast cancer. In addition, the accurate analysis and quantification of T4 and T3 is an issue recognized by those skilled in the art. The presence of circulating iodothyronine-binding autoantibodies that interfere with total T4 and T3 immunoassays ("IAs") is a known phenomenon [2], [3], [4]. These autoantibodies may give falsely high, or falsely low values of thyroid hormone measurements depending on the assay separation method used, and are often in discordance with the clinical features [2], [3], [4]. Serum free T4 and T3 (FT4 and FT3) measurements are a way to compensate for such abnormal binding. However, technically, it is difficult to measure the free hormone concentrations since these are so low. It is easier to measure the total (free and protein-bound) thyroid hormone concentrations; total hormone concentrations are measured at nanomolar levels whereas free hormone concentrations are measured in the picomole range and to be valid, must be free from interference by the much higher total hormone concentrations.

Presently, the common methods of hormone analysis use immunoassay techniques. Table 1 lists the common hormones and the current methods for their analysis.

For example, estriol is analyzed by a radioimmunoassay utilizing radiolabelled antigen (iodine 125) in competition with unlabelled estriol in the sample, for a known amount of antibody. The assay is read using a gamma counter.

Androstenedione is analyzed using an enzyme immunoassay comprising horseradish peroxidase. Unlabeled antigen in the sample is in competition with enzyme labeled antigen for a fixed number of antibody binding sites. The assay is read using a microtitre plate enzyme immunoassay reader.

Several hormones are currently analyzed using a chemiluminescent immunoassay. For example, progesterone, testosterone, cortisol and T3 are analyzed using this method. The assay utilizes an assay-specific antibody-coated bead. The assay is read using a photon counter.

However, the current immunoassays are disadvantageous for the following reasons:
(1) Immunoassays are specific to one hormone, therefore every hormone must be analyzed separately.
(2) Numerous kits must be purchased and procedures must be learned for each hormone being analyzed.
(3) Various instruments to read the results from the immunoassays must be purchased.

For example, the analysis of estriol and progesterone from a sample requires both a gamma counter and a photon counter.
(4) The kits for the assays can be expensive.
(5) The current immunoassays lack specificity and may show approximately 15 fold difference in results using kits from different manufacturers [5].
(6) The procedures involve many steps and can take a significant amount of time.
(7) In the case of a radioimmunoassay, precautions are necessary because of the radioisotopes involved.

Immunoassays are notoriously unreliable with more and more literature published supporting their lack of specificity [6-13]. Table 2 shows the major differences reported by the College of American Pathologists program for proficiency testing of thyroid hormones that clearly illustrates the difference in specificity of the various antibodies used. For example, Table 2 shows mean results between different methods reported in the College of American Pathologists Proficiency Testing (CAP PT) Program can vary by a factor of approximately 2. Some factors such as pregnancy, estrogen therapy or genetic abnormalities in protein binding have also reportedly made immunoassay methods for T4 and T3 diagnostically unreliable [2], [3], [14], [15]. Currently serum total free T4 (FT4) and free T3 (FT3) concentrations are most commonly measured by immunoassay methods. Recently some reports of quantitative measurement of T4 and T3 by high performance liquid chromatography (HPLC), gas chromatography mass spectrometry (GC-MS), liquid chromatography mass spectrometry (LC-MS) or tandem mass spectrometry (LC-MS/MS) were published [16-20]. All those methods required extraction, derivatization and even prior chromatographic separation that are very time-consuming [21], [22].

More recently, hormones have been analyzed and quantified by mass spectrometry. However, there are several disadvantages to these methods.

For example, a method of analyzing urinary testosterone and dihydrotestosterone glucuronides using electrospray tandem mass spectrometry has been described [23]. The method involves a complex system employing high performance liquid chromatography (HPLC) and a three-column two-switching valve. The shortcomings include the following: (i) the hormone glucuronides were analyzed, not the hormones, (ii) the method is applicable to urine only and (iii) only two analytes were analyzed simultaneously, (iv) the limit of detection (LOD) was 200 pg ml$^{-1}$ for testosterone and the limit of quantification was 10 ug L$^{-1}$ for dihydrotestosterone and (v) the method is complex.

Another publication discloses a method for the determination of estradiol in bovine plasma by an ion trap gas chromatography-tandem mass spectrometry technique [24]. The shortcomings include the following: (i) only one analyte was analyzed, (ii) 4 ml of plasma was required for the analysis of one analyte, (iii) the limit of detection was 5 pg ml$^{-1}$, and (iv) derivation was required because the method employs gas chromatography.

A method for analysis of 17-hydroxyprogesterone by HPLC electrospray ionization tandem mass spectrometry from dried blood spots has also been described [25]. However, this method analyses only one analyte at a time, and requires liquid-liquid extraction, which is laborious and time consuming, with sample extraction alone taking 50 minutes to complete.

A gas chromatography mass spectrometry method to analyze the production rates of testosterone and dihydrosterone has been disclosed [26].

Finally, there is no known method of analyzing free thyroxine (FT4) or free triiodothyronine (FT3) by mass spectrometry. Most laboratories perform FT4 testing routinely employing the analogue (direct) immunoassay approach on one of the major clinical chemistry platforms. This approach is not universally accepted and has been the subject of criticism (29). There are frequent occasions when the validity of the FT4 result generated in this manner is questioned. For this reason a "reflex" testing for all direct FT4's<2.5$^{th}$ percentile is often done to diagnose hypothyroidism. These are sent out for FT4 measurements employing the current gold standard of equilibrium dialysis. This is also done for samples when the direct FT4 is >97.5$^{th}$ percentile and the TSH is normal. Approximately 50% of these FT4 send-outs have results within the normal range when measured by equilibrium dialysis and are therefore false positives by the direct FT4 method. However, the equilibrium dialysis procedures are time-consuming and expensive. Similarly, FT3 is also currently measured by immunoassay.

TABLE 1

METHODS AND INSTRUMENTS FOR STEROID AND THYROID HORMONES [1]

| Analyte | Percentage of Use | Instrument | Method |
|---|---|---|---|
| Androstenedione | 35% | DSL solid | EIA |
| 11-Deoxycortisol | 50% | ICN Immuchem DA | RIA |
| DHEA Sulfate | 39% | DPC Immulite | ECIA |
| Estradiol | 16% | Bayer ADVIA Centaur | FIA |
| Estriol, unconjugated | 25% | DSL liquid | RIA |
| Estriol, Total | 50% | DPC Coat-a-Count | RIA |
| 17-Hydroxy-progesterone | 51% | DPC Coat-a-Count | RIA |
| Progesterone | 23% | Bayer ADVIA Centaur | CIA |
| Testosterone | 29% | Bayer ADVIA Centaur | CIA |
| Testosterone, Free | 65% | DPC Coat-a-Count | RIA |
| Aldosterone | 76% | DPC Coat-a-Count | RIA |
| Cortisol Corticosterone | 25% | Bayer ADVIA Centaur | CIA |
| T3 | 29% | Abbott Axsym | FPIA |
| T3, Free | 31% | Bayer ADVIA Centaur | CIA |
| T4 | 30% | Abbott Axsym | FPIA |
| T4, Free | 34% | Abbott Axsym | FPIA |

RIA: Radioimmunoassay
EIA: Enzyme Linked Immunoassay
FPIA: Fluorescence Polarization Immunoassay

TABLE 2

Problems with Immunoassays: Data acquired from CAP PT Program 2003

| Analyte | Mean CAP Result for Method Giving Lowest Value | Mean CAP Result for Method Giving Highest Value |
|---|---|---|
| Triiodothyronine (ng/dL) | 108.5 | 190.2 |
|  | 364.8 | 610.1 |
| Thyroxine (ug/dL) | 5.64 | 10.09 |
|  | 1.64 | 3.65 |
|  | 8.73 | 13.12 |

SUMMARY

The applicant's teaching provides a fast and accurate method of hormone analysis and quantification using a mass spectrometer.

A plurality of hormones can be analyzed simultaneously or sequentially. The procedure allows for as little as 100 μL of a sample to be analyzed. In addition, minimal sample preparation time is required.

The applicant's teaching permits the analysis of hormones in a number of complex matrices as they might be found in nature, e.g. the human body. For, example, hormone analysis can be performed on samples of blood, saliva, serum, plasma and urine.

There are several features to this teaching:
(1) It provides a total and specific analysis for hormones in a sample. The present method allows for the analysis of many hormones simultaneously or sequentially.
(2) The procedure does not require an immunoprecipitation reaction. The majority of other methods for hormone analysis required an immunoassay. Immunoassays are expensive, specific to a particular analyte and involve several steps.
(3) The present teaching requires minimal sample preparation time. For example, preparing a sample for hormone analysis can be done within 6 minutes.

(4) The procedure does not require a large sample size. A plasma or serum sample can be as small as 100 µL for thyroid hormones. For FT4 and FT3 the sample can be between 500 and 600 µL. The current methods for hormone analysis that utilize mass spectrometry require 4-15 mL of plasma.

(5) The methods use simple preparation techniques that are easy to use and highly reproducible.

(6) The methods permit analysis to be performed on a variety of sample types.

(7) The methods permit the analysis of hormones in a sample of saliva or urine which permits simple sample acquisition and the remote submission of samples to a clinic for analysis. In previous other clinical methods, samples are taken by invasive means directly from the patient in a clinic.

(8) The analysis by mass spectrometry is highly accurate. In addition, the procedure of the present methods are highly reproducible.

(9) The methods permit the analysis of a wide range of hormone concentrations. In addition, the limit of detection can be fairly low.

Accordingly, there is provided a method for mass spectrometric analysis of a sample containing or suspected of containing free thyroxine (FT4) hormone, comprising the steps (a) providing a sample containing or suspected of containing FT4 hormone, (b) separating FT4 hormone from the sample, (c) collecting FT4 hormone, and (d) analyzing FT4 hormone using a mass spectrometer.

Accordingly, there is provided a method for mass spectrometric analysis of a sample containing or suspected of containing free triiodothyronine (FT3) hormone, comprising the steps (a) providing a sample containing or suspected of containing FT3 hormone, (b) separating FT3 hormone from the sample, (c) collecting FT3 hormone, and (d) analyzing FT3 hormone using a mass spectrometer.

Accordingly, there is provided a method for mass spectrometric analysis of a sample containing or suspected of containing free thyroxine (FT4) and free triiodothyronine (FT3) hormone, comprising the steps (a) providing a sample containing or suspected of containing FT4 and FT3 hormone, (b) separating FT4 and FT3 hormone from the sample, (c) collecting FT4 and FT3 hormone, and (d) analyzing FT4 and FT3 hormone using a mass spectrometer.

There is also provided a method of instructing an analysis of a sample that comprises or is suspected of comprising FT4 and/or FT3 hormone. The method comprises providing instructions to prepare and analyze the sample, as described above.

Accordingly, there is provided a system for the mass spectrometric analysis of a sample containing or suspected of containing FT4, comprising (a) reagents for separating FT4 from the sample, including internal standards, (b) reagents for analyzing FT4 hormone using a mass spectrometer, and (c) a mass spectrometer.

Accordingly, there is provided a system for the mass spectrometric analysis of a sample containing or suspected of containing FT3, comprising (a) reagents for separating FT3 from the sample, including internal standards, (b) reagents for analyzing FT3 hormone using a mass spectrometer, and (c) a mass spectrometer.

Accordingly there is provided a kit for use in mass spectrometric analysis of a sample containing or suspected of containing FT4, comprising (a) reagents for separating FT4 from the sample, (b) reagents for analyzing the FT4 using a mass spectrometer, (c) a solution of FT4, and (d) instructions for analyzing the FT4 using a mass spectrometer.

Accordingly there is provided a kit for use in mass spectrometric analysis of a sample containing or suspected of containing FT3, comprising (a) reagents for separating FT3 from the sample, (b) reagents for analyzing the FT3 using a mass spectrometer, (c) a solution of FT3, and (d) instructions for analyzing the FT3 using a mass spectrometer.

There is also provided a kit for use in mass spectrometric analysis of a sample containing or suspected of containing FT4 and FT3, comprising (a) reagents for separating FT4 and FT3 from the sample, (b) reagents for analyzing the FT4 and FT3 using a mass spectrometer, (c) a solution of FT4 and FT3, and (d) instructions for analyzing the FT4 and FT3 using a mass spectrometer.

Accordingly there is provided use of a mass spectrometer for analyzing a sample containing or suspected of containing FT4, FT3 or both.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

The methods, including the best approaches known to the inventors, can be better understood with reference to the following description taken in combination with the following drawings, in which.

DESCRIPTION OF VARIOUS EMBODIMENTS

Figure 1:
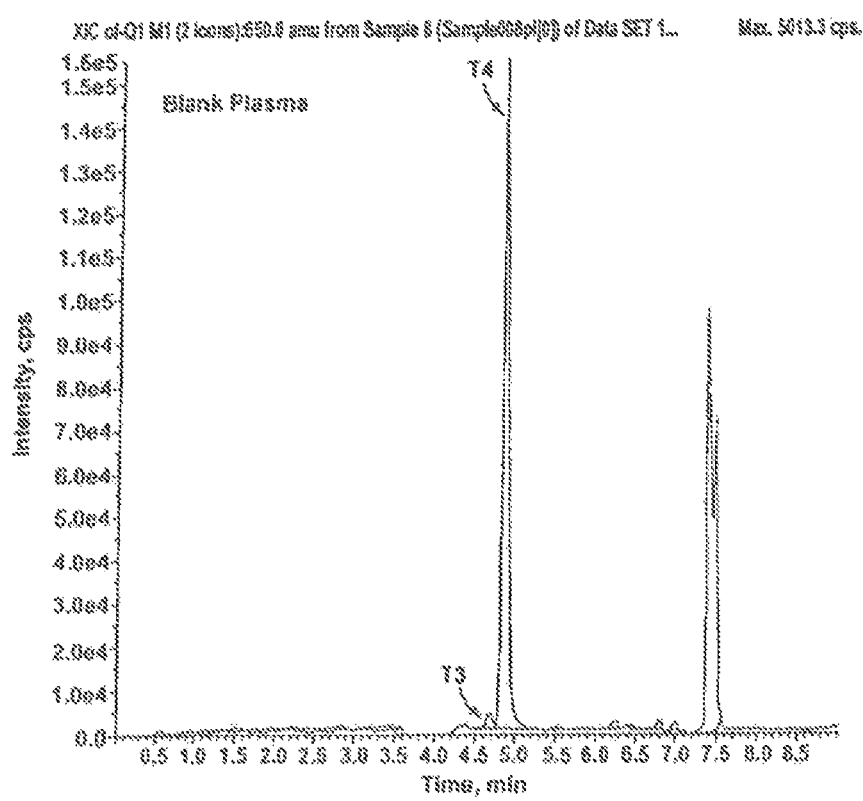
FIG. 1 is a mass spectrum of a sample of plasma containing T4 and T3.

The applicant's teaching provides methods of analysis for hormones. The hormones may include:

Dehydroepiandrosterone (DHEA)
Dehydroepiandrosterone sulphate (DHEAS)
Aldosterone
Cortisol
Corticosterone
11-Deoxycortisol Androstenedione
Testosterone
Estradiol
17-OH Progesterone
Progesterone
Allopregnanolone
16OH Estrone
2-OH Estrone
Estrone
Estriol
Vitamin D, and its metabolites 25hydroxyvitamin D and 1,25 dihydroxyvitamin D. thyroxine
   free thyroxine
   triiodothyronine
   free triiodothyronine
   catecholamines
   metanephrines
   other steroid hormones
   other thyroid hormones
   other small peptide hormones
   other amines Sample Any sample containing or suspected of containing a hormone can be used, including a sample of blood, plasma, serum, urine or saliva. The sample may contain both free and conjugated or bound hormones. A sample size of at least about 100 μL for hormones generally, or at least about 700 μL for steroid hormones when using API 3000™, or 200 to 500 μL for steroid hormones when using the API 4000™ or API 5000™, can be used. A sample size of 500 to 600 μL for FT4 and FT3 can be used when using the API 4000™ or API 5000™.

Deproteinization

The sample may be de-proteinated. This can be done by conventional techniques known to those skilled in the art. For example, a sample can be de-proteinated with acetonitrile, containing internal standard, followed by vortexing and centrifugation. The internal standard may be, for example, the deuterated hormone.

Separation of Hormones from the Sample

The hormones are separated by methods known to those skilled in the art. For example, the hormones may be separated by liquid chromatography through a column. Many different columns can be used. For example, the column may be a C-18 column or, for example, a C-8 column. The column may also be a C6, C4, C2 or similar column. As is known to those skilled in the art, the shorter the carbon chain, the shorter the retention time. The hormones are subsequently eluted from the column.

The hormones may also be separated by centrifugation. For example, FT4 may be separated from other compounds, including bound T4 by centrifugation using an ultrafiltration device. After centrifugation, the ultrafiltrate will contain FT4, while the bound T4 and other compounds will be unable to pass through the filter. Alternatively, the hormones may be separated by equilibrium dialysis or other methods known to those skilled in the art.

Introduction of Hormones into a Mass Spectrometer

The hormones are then introduced into a mass spectrometer. Optionally, the separation step and step of introducing the hormones into a mass spectrometer can be combined using a combined liquid chromatography spectrometry apparatus (LC/MS). This procedure is based on an online extraction of the injected sample with subsequent introduction into the mass spectrometer using a built-in switching valve.

Isotope Dilution Tandem Mass Spectrometry

The methods employ isotope dilution mass spectrometry.

Instrumentation and Ionization Techniques

The hormones are subjected to ionization. Various ionization techniques can be used. For example, photoionization, electrospray ionization (ESI), atmospheric pressure chemical ionization (APCI), and electron capture ionization may be used. Electrospray ionization can be utilized when analyzing thyroid hormones.

The following mass spectrometers can be used: any tandem-mass spectrometer, including hybrid quadrupole-linear ion trap mass spectrometers and liquid chromatography-tandem mass spectrometers such as the API 3000™ mass spectrometer and the API 4000™ mass spectrometer, described in U.S. Pat. Nos. 4,121,099; 4,137,750; 4,328,420; 4,963,736; 5,179,278; 5,248,875; 5,412,208; and 5,847,386 (Applied Biosystems/MDS SCIEX, Foster City, Calif./Concord Ontario, Canada). When analyzing thyroid hormones, a spectrometer with a turbo spray ion source, such as the API 2000™ and API 3000™ mass spectrometers can be used. When analyzing FT4, the API $4000^{th}$ mass spectrometer can be used. When analyzing FT3, the API 5000™ mass spectrometer can be used. When analyzing FT3 and FT4 simultaneously the API $5000^{th}$ mass spectrometer can be used.

Ionization may be performed by utilizing the mass spectrometer in the negative or the positive mode, depending on a particular analyte's tendency to give rise to a particular ion form, as is known to those skilled in the art. Typically, for thyroid hormones, the spectrometer is employed in the negative mode.

Hormones are identified on the basis of the mass to charge ratio of their molecular ions and fragment ions, as is known to those skilled in the art. When the hormones are purified by liquid chromatography, they can also be identified by their retention times.

Hormones are quantified by their intensity as determined in the mass spectrometer in counts per second. Calibration curves for known concentrations of the hormones are established for comparison.

Kits

Kits for use in mass spectrometric analysis of a sample comprising or suspected of comprising FT4, FT3 or both are also provided. The kits are assembled as is known to those skilled in the art. The kits can comprise, for example, reagents for separating the hormone from the sample, reagents for analyzing the hormone using a mass spectrometer, a solution of the hormone, and instructions.

EXAMPLES

Aspects of the applicant's teachings may be further understood in light of the following examples, which should not be construed as limiting the scope of the present teachings in any way.

1. Analysis of a Sample for Thyroid Hormones

A sample of 100 μL of plasma was used. Proteins were precipitated with 150 μL of acetonitrile, capped and vortexed. The sample was then centrifuged, and 200 μL of the supernatant was injected onto a Supelco LC-18-DB™ chromatographic column equipped with Supelco Discovery C-18™ guard column, coupled to a tandem mass spectrometer (LC/MS/MS). The column was washed with 20% methanol in 5 mM ammonium acetate for 3 minutes. The valve was switched and the sample was eluted in 75% to 95% methanol. The total run time was 6 minutes. Slight adjustments to the volumes, concentrations and times described can be made, as is known to those skilled in the art.

The eluant was introduced into an ion-spray ionization chamber and analyzed by API 2000™ mass spectrometer using the negative mode. The mass/charge ratios for T4 and T3 ions is 775.8 and 650 respectively. The ionization may be by electrospray using a turboionspray chamber.

This demonstrates a simple method of preparing a complex biological matrix for analysis of hormone content, and a sensitive analytical method that permits the simultaneous analysis of two hormones, T3 and T4.

2. Analysis of Thyroid Hormones using a Methanol Gradient to Elute the Hormones

A sample of 100 μL of plasma was used. Proteins were precipitated with 150 μL of acetonitrile, containing an internal standard of deuterated $T_4$ and vortexed. The sample was centrifuged, and 200 μL of the supernatant was injected onto a C-18 column coupled to a tandem mass spectrometer (LC/MS/MS). The column was washed with 20% methanol in 5 mM ammonium acetate for 3 minutes. The valve on the column was switched and the sample was eluted in a methanol gradient of 20 to 100%. The total run time was 7 minutes. Slight adjustments to the volumes, concentrations and times described can be made by those skilled in the art.

Figure 2:
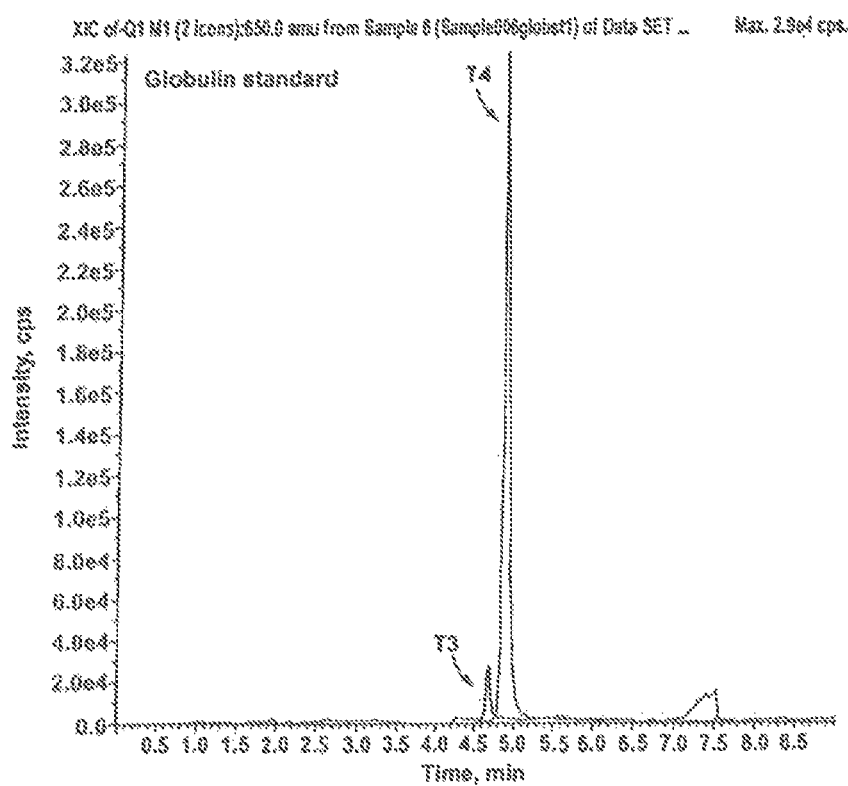
FIG. 2 is a mass spectrum of a globulin standard containing T4 and T3.

A sample of the eluant was introduced into an ion-spray ionization chamber and analyzed by an API 3000™ mass spectrometer using the negative mode. The ionization may be by electrospray using a turboionspray chamber. FIG. 1 and FIG. 2 shows the mass spectrums generated for T3 and T4.

This demonstrates a simple method of preparing a complex biological matrix for analysis of thyroid hormone content, and a sensitive analytical method that permits the simultaneous analysis of multiple hormones.

3. Analysis of Thyroid Hormones using Isotope Dilution Tandem Mass Spectrometry

This example describes an isotope dilution tandem mass spectrometry method for the simultaneous determination of T4 and T3 in serum. The method is accurate, specific, precise (% CVs between 3.5 and 9.0), simple—requiring no extraction and only protein precipitation, and fast. For example it can be done in less than seven minutes.

Chemicals and Reagents

Standards of T4 and T3 were purchased from Sigma (St. Louis, Mo., USA). A stable deuterium-labeled internal standard, L-thyroxin-$d_2$ was synthesized according to procedures described in the literature [16], [17] by Dr Tomas Class from the Chemistry Department at Georgetown University. HPLC grade methanol was purchased from VWR Scientific. All other chemicals were of analytical grade and purchased from Sigma.

Solutions and Standards

Stock solutions of T3, T4 and internal standard (IS) were prepared separately to obtain a concentration of 1 mg/mL for each. 40% ammonium hydroxide (v/v) in methanol was used as a solvent. The analyte stock solutions were diluted with methanol to obtain the spiking solutions. The solutions were stored at 4° C. and could be used for several months. Standards for the calibration curve in the range of 0.325 to 5 ng/mL for T3 and 12.5 to 200 ng/mL for T4 were prepared by adding the analyses to 3% human γ-globulin (volume of spiking solution<2% of fmal volume). Quality control (QC) samples (Diagnostic Product Corp., Los Angeles, USA) at low, medium and high levels were used. A solution of 50-ng/mL $d_2$-T4 in methanol was used as the internal standard.

Sample Preparation

Serum or plasma samples were thawed at room temperature. 150 μL of IS solution was added to aliquots of 100 μL of the serum or plasma sample. After 30 seconds of vortex mixing, the samples were stored for 10 minutes at room temperature to allow complete protein precipitation. The samples were centrifuged for 10 minutes at 15,000 rpm and 100 μl of supernatant was injected into the LC-MS-MS system.

LC/MS/MS Conditions

An API 3000™ tandem mass-spectrometer (SCIEX, Toronto, Canada) equipped with TurboIonSpray and Shimadzu HPLC system was used to perform the analysis. Negative ion multiple reaction-monitoring (MRM) mode was used. The transitions to monitor were selected at m/z 650→127 for T3, m/z 776→127 for T4, m/z 778→127 for $d_2$-T4. Nitrogen served as auxiliary, curtain and collision gas. Gas flow rates, source temperature, Ion Spray voltages and collision energies were optimized for every compound by infusion of 1 μg/mL of the standard solutions in methanol at 20 μL/min and by flow-injection analysis (FIA) at LC flow rate. The main working parameters for the mass spectrometer are summarized in Table 3. Data processing was performed on Analyst 1.2 software package.

LC-MS-MS Procedure

The procedure used is based on an online extraction/cleaning of the injected samples with subsequent introduction into the mass-spectrometer by using a built-in Valco switching valve. 100 μl of the sample was injected onto a Supelco LC-18-DB (3.3 cm×3.0 mm, 3.0 μm ID) chromatographic column equipped with a Supelco Discovery C-18 (3.0 mm) Guard column, where it underwent cleaning with 20% (v/v) methanol in 5 mM ammonium acetate pH=4.0 at flow rate 0.8 mL/minute. After 3.5 minutes of cleaning the switching valve was activated, the column was flushed with water/methanol gradient at flow rate 0.5 mL/min and the samples were introduced into the mass-spectrometer. The gradient parameters used are shown in Table 4.

Immunoassays for T4 and T3

T4 was measured by the Dade RxL Dimension™ (Dade-Behring Diagnostics, Glasgow, Del.) and T3 by the DPC Immulite™ (Diagnostic Product Corporation, Los Angeles, Calif.) according to the manufacturer's specifications.

Results

The mass spectrometer working parameters used are shown in Tables 3 and 4.

Replicate sera were assayed both within-day and between-day at several concentrations. The within-day and between-day precision data is provided in Tables 5 and 6.

Recovery studies for T4 and T3 are shown in Tables 7 and 8. All results shown are the means of 8 replicates.

Figure 3:
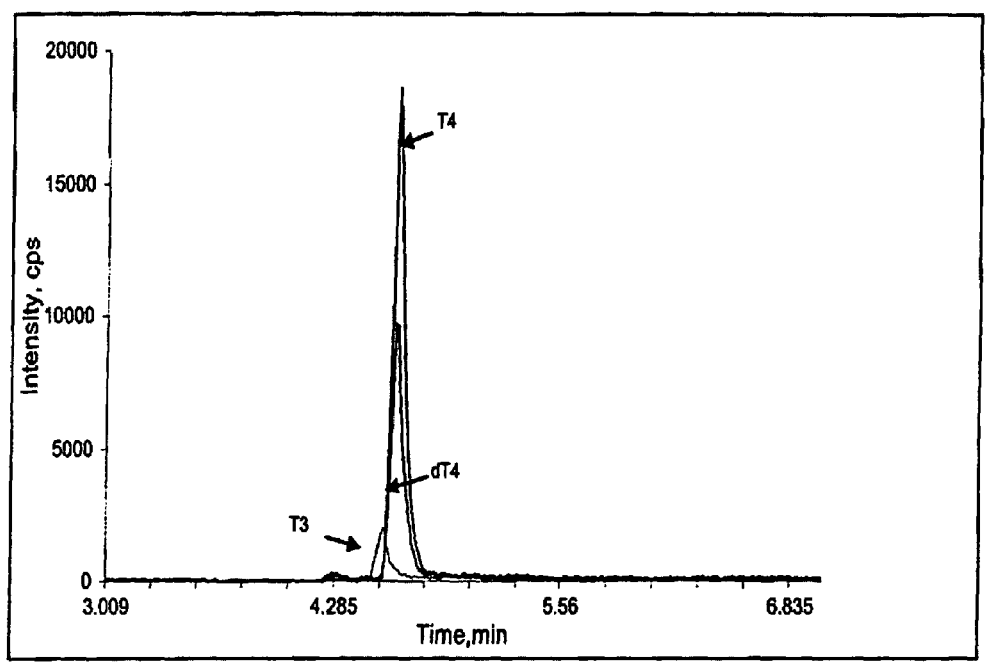
FIG. 3 is a typical tandem mass spectrometric chromatogram obtained for T4 and T3 for a plasma sample. T4 m/z (776/127); $D_2T4$ m/z (778/127); T3 m/z (650/127)

FIG. 3 shows a typical tandem mass spectrometric chromatogram obtained for T3 and T4 (T4 m/z (776/127); $D_2$T4 m/z (778/127); T3 m/z (650/127)).

Figure 4:
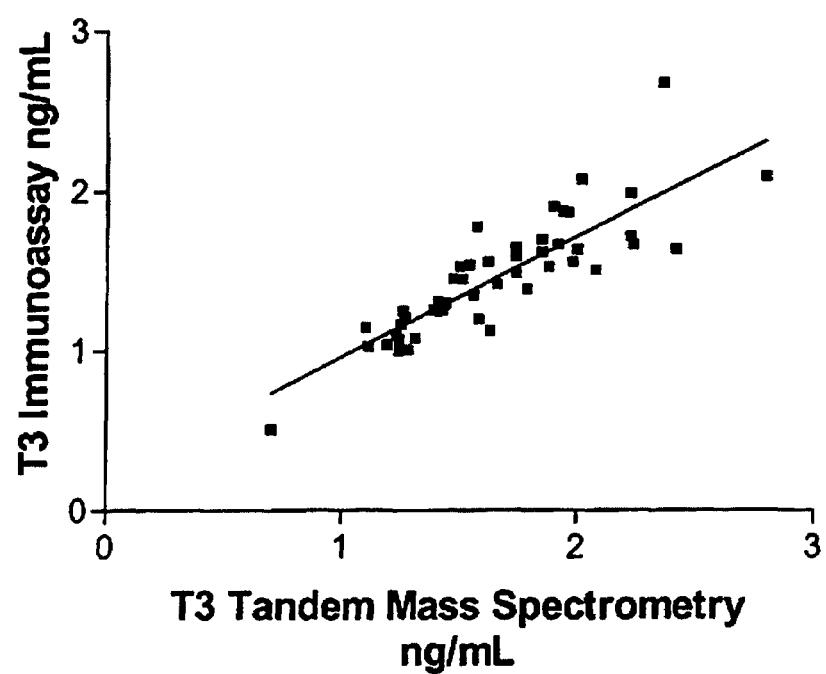
FIG. 4 is a graph showing T3 measured by Isotope Dilution Tandem Mass Spectrometry vs. Immunoassay. IA=075 MS+0.21; r=0.848; $S_{y,x}$=0.1956; n=49.
Figure 5:
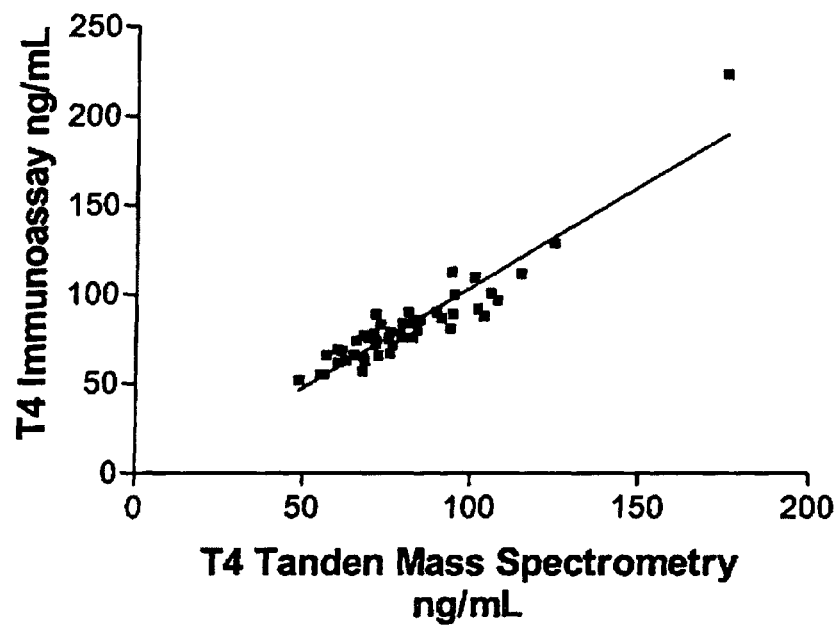
FIG. 5 is a graph showing T4 measured by Isotope Dilution Tandem Mass Spectrometry vs. Immunoassay. IA=1.13 MS-8.99; r=0.931; $S_{y,x}$=9.54; n=50

Specimens were tested for T3 and T4 by both immunoassay (T3 DPC Immulite, T4 Dade Behring Dimension™ RxL) and by tandem mass spectrometry. Linear regression correlations (Prism) are shown in FIGS. 4 and 5.

The lower limit of quantitation of the mass spectrometry method was found to be 0.15 ng/mL for both T3 and T4. Detection limit was around 0.062 ng/mL.

Discussion

Evidence initially gleaned from both the CAP PT Program and pediatric reference ranges employing different immunoassays indicated the probability of lack of specificity for T4 and T3 immunoassay tests. To adequately assess this phenomenon, the isotope dilution tandem mass spectrometric method was developed as described in this example. Serum T4 and T3 detection methods have evolved through a variety of technologies since the 1950s. Radioimmunoassay (RIA) methods to detect thyroid hormones were developed in the 1970s. Serum T4 and T3 concentrations are currently measured by competitive immunoassay methods (IAs) that are mostly non-isotopic and use enzymes, fluorescence or chemiluminescence molecules as signals [27]. Table 2 clearly indicates that current IAs for T4 and T3 lack specificity and give mean results differing by a factor of approximately 2 in the College of American Pathologists Proficiency Testing (CAP PT) programs. Total hormone assays necessitate the inclusion of a displacing agent (such as salicylate) to release the hormone from its binding proteins [28]. The displacement of hormone binding from serum proteins by such agents, together with the large sample dilution employed in modern assays, facilitates the binding of hormone to the antibody reagent.

Since T3 is ten-fold lower in concentration compared with T4 in blood it therefore presents both a technical sensitivity and precision challenge despite the use of a higher specimen volume. Although a reliable high-range T3 measurement is critical for diagnosing hyperthyroidism, a reliable normal-range measurement is also important for adjusting antithyroid drug dosage and detecting hyperthyroidism in sick hospitalized patients, in whom a paradoxically normal T3 value may indicate hyperthyroidism.

The correlation coefficient for the T4 comparisons (0.931) is significantly better than for the T3 comparisons (0.848) (FIGS. 4 and 5). T3 by tandem mass spectrometry gave slightly higher results than those obtained by the DPC Immulite™ (FIG. 4). While this is true for children, preliminary data for non-pregnant and pregnant women indicates a very poor correlation for T3 in both groups (r between 0.407-0.574) (i.e. there is a poor correlation between DPC Immulite and the method of the present teaching in both non-pregnant and pregnant women).

The reasons for this are not clear but could include standardization issues, heterophilic antibodies, etc. Of importance, reverse T3, which lacks a daughter ion of 127 m/z, does not interfere in the tandem mass spectrometry methods. Applying the tandem mass spectrometric method to CAP PT samples in the K/KN (thyroid) general ligand program again revealed that around 85% of the immunoassay methods for T3 gave means on samples which were lower than the means obtained by the tandem mass spectrometry methods of this applicant's teaching while 15% had higher means. For T4, the tandem mass spectrometry method resulted in lower means than those of the immunoassay methods.

In conclusion, correlations between immunoassays and tandem mass spectrometry for T4 and T3 have been demonstrated. The correlation is better for T4 than for T3. Further, the correlation is less impressive during pregnancy. Recovery studies from several different sera using deuterated T4 as internal standard showed consistent (90-109%) recoveries for both T4 and T3 (Tables 7 and 8). The recovery differences found between samples were surprisingly larger for T4 than for T3. This indicates a lack of need to use deuterated T3 as the T3 internal standard. The isotope dilution tandem mass spectrometric method of the applicant's teaching is rapid (less than 7 minutes), accurate (provides the true result as has been assessed by recovery studies), specific (measures only the analyte it purports to measure), precise (low % CV) and easy to perform.

TABLE 3

Tandem mass-spectrometer working parameters

| Parameter | Value | |
|---|---|---|
| Nebulizer gas (NEB) | 8 | |
| Curtain gas (CUR) | 10 | |
| Collision gas (CAD) | 6 | |
| TurboIon Spray Heater gas | 7 | L/min |
| TurboIon Spray (IS) voltage | 4500 | V |
| Entrance Potential (EP) | 7.5 | V |
| Collision cell Exit Potential (CXP) | 5 | V |
| Source temperature | 450° | |
| Dwell time | 250 | msec |

TABLE 4

Gradient parameters

| Time (min) | Methanol (%) |
|---|---|
| 3.50 | 75 |
| 5.25 | 76 |
| 5.50 | 100 |
| 7.00 | End |

TABLE 5

Within day precision (n = 10)

| | CONTROL 1 | | | CONTROL 2 | | |
|---|---|---|---|---|---|---|
| Analyte | Mean (ng/mL) | SD | CV (%) | Mean (ng/mL) | SD | CV (%) |
| T3 | 1.04 | 0.014 | 1.36 | 2.44 | 0.077 | 3.19 |
| T4 | 24.1 | 0.437 | 1.81 | 81.2 | 1.502 | 1.85 |

TABLE 6

Between day precision (n = 20, 1 run per day for 20 days)

| | CONTROL 1 | | | CONTROL 2 | | | CONTROL 3 | | |
|---|---|---|---|---|---|---|---|---|---|
| Analyte | Mean (ng/mL) | SD | CV (%) | Mean (ng/mL) | SD | CV (%) | Mean (ng/mL) | SD | CV (%) |
| T3 | 1.08 | 0.05 | 4.47 | 2.39 | 0.22 | 9.21 | 3.49 | 0.31 | 9.00 |
| T4 | 24.4 | 1.39 | 5.69 | 76.6 | 3.11 | 4.06 | 116.3 | 4.15 | 3.57 |

TABLE 7

Recovery of added thyroxine (T4)

| Sample # | Added (ng/mL) | Detected mean | Added amount recovered | Recovery, % |
|---|---|---|---|---|
| 1 (n = 8) | 0 | 85.9 | NA* | NA |
| | 10 | 96.7 | 10.8 | 108.0 |
| | 40 | 127.5 | 41.6 | 104.0 |

TABLE 7-continued

Recovery of added thyroxine (T4)

| Sample # | Added (ng/mL) | Detected mean | Added amount recovered | Recovery, % |
|---|---|---|---|---|
| 2 (n = 5) | 0 | 62.6 | NA | NA |
| | 10 | 72.1 | 9.5 | 95.0 |
| | 40 | 98.0 | 35.4 | 90.0 |
| 3 (n = 5) | 0 | 73.8 | NA | NA |
| | 10 | 84.7 | 10.9 | 109.0 |
| | 40 | 116 | 42.2 | 105.0 |
| 4 (n = 5) | 0 | 58.3 | NA | NA |
| | 10 | 68.0 | 9.7 | 97.0 |
| | 40 | 95.0 | 36.7 | 92.0 |

*NA—not applicable

TABLE 8

Recovery of added triiodothyronine (T3)

| Sample # | Added (ng/mL) | Detected mean | Added amount recovered | Recovery, % |
|---|---|---|---|---|
| 1 (n = 8) | 0 | 1.88 | NA | NA |
| | 0.25 | 2.12 | 0.24 | 96.0 |
| | 1.00 | 2.85 | 0.97 | 97.0 |
| 2 (n = 5) | 0 | 1.70 | NA | NA |
| | 0.25 | 1.96 | 0.26 | 104.0 |
| | 1.00 | 2.76 | 1.06 | 106.0 |
| 3 (n = 5) | 0 | 1.56 | NA | NA |
| | 0.25 | 1.81 | 0.25 | 100.0 |
| | 1.00 | 2.62 | 1.06 | 106.0 |
| 4 (n = 5) | 0 | 0.49 | NA | NA |
| | 0.25 | 0.74 | 0.25 | 100.0 |
| | 1.00 | 1.50 | 1.01 | 101.0 |

*NA—not applicable

4. Analysis of Free Thyroxine (FT4)

Most routine clinical chemistry service laboratories provide for the measurement of free thyroxine (FT4) by an analogue (direct) method with 24 hours and 7 day per week availability. Nevertheless, the validity of analogue FT4 immunoassays has long been questioned and patient's results using this approach frequently do not fit in with the clinical picture. Because of this, direct free T4's that are below the 2.5$^{th}$ percentile and many that are above the 97.5$^{th}$ percentile are often sent for further measurement by the current "gold standard" method for FT4, equilibrium dialysis. In approximately 50% of these cases the FT4 by equilibrium dialysis has been found to be normal. The present methods teach a rapid, reliable free T4 method employing isotope dilution tandem mass spectrometry and compares results obtained by this method with both the analogue (direct) free T4 and the time-consuming and relatively expensive equilibrium dialysis procedures.

Methods:
Chemicals and Reagents

Thyroxine (T4) was purchased from Sigma (St Louis, Mo.). A stable deuterium-labeled internal standard, L-thyroxin-$d_2$ was synthesized according to procedures described in the literature (29, 30) by Dr Tomas Class from the Chemistry Department at Georgetown University. HPLC grade methanol was purchased from VWR Scientific. All other chemicals were of analytical grade and were purchased from Sigma.

Solutions and Standards

Stock solutions of T4 and internal standard (IS) were prepared separately to obtain concentration of 10 mg/mL for each using 40% ammonium hydroxide (v/v) in methanol as a solvent. The analyte stock solutions were diluted with methanol to obtain the spiking solutions. The solutions were stored at -20° C. and could be used for several months. Standards for the T4 calibration curve in the range of 2.5-50 pg/mL were prepared by adding the analytes to water. A solution of 0.05 ng/mL $d_2$-T4 in methanol was used as internal standard.

Sample Preparation

Serum or plasma samples were obtained from greater than 42 healthy pregnant and 29 non-pregnant women in a study approved by the Institutional Review Board (IRB) and were thawed at room temperature. 0.6 ml samples were filtered through Centrifree YM-30 ultrafiltration devices (30,000 MW cut-off, Millipore, Bedford, Mass.) by centrifugation employing the Eppendorf temperature controlled centrifuge (model # 5702 R, Eppendorf, AG, Hamburg) and using a fixed angle rotor at 2900 rpm and a temperature of 25° for 1 hour. 180 μL IS [0.05 ng/mL] was added to 360 μL ultrafiltrate and 400 μL was injected onto the C-18 column of the LC/MS/MS system. This ultrafiltration process replaces the dialysis step of the classic equilibrium dialysis method. The ultrafiltration step includes removal of all proteins having a molecular weight of greater than 30,000. The liquid chromatography step can be used to further separate and purify the hormone.

LC/MS/MS Setup

An API 4000™ tandem mass-spectrometer (SCIEX, Toronto, Canada) equipped with TurboIonSpray and Agilent 1100 HPLC system was used to perform the analysis. Negative ion multiple reaction-monitoring (MRM) mode was used. The transitions to monitor were selected and are m/z 775.9→126.9 for T4, m/z 777.9→126.9 for $d_2$-T4. Nitrogen served as auxiliary, curtain and collision gas. Gas flow rates, source t°, Ion Spray voltages and collision energies were optimized for every compound by infusion of 1 μg/mL standards solutions in methanol at 20 μL/min and by flow-injection analysis (FIA) at LC flow rate. The main working parameters of mass spectrometer used are summarized in Table 9. Data processing was performed on Analyst 1.4.1 software package. Although the negative mode was used in this example, a positive mode can be used but is less sensitive.

LC-MS-MS Procedure

Figure 6:
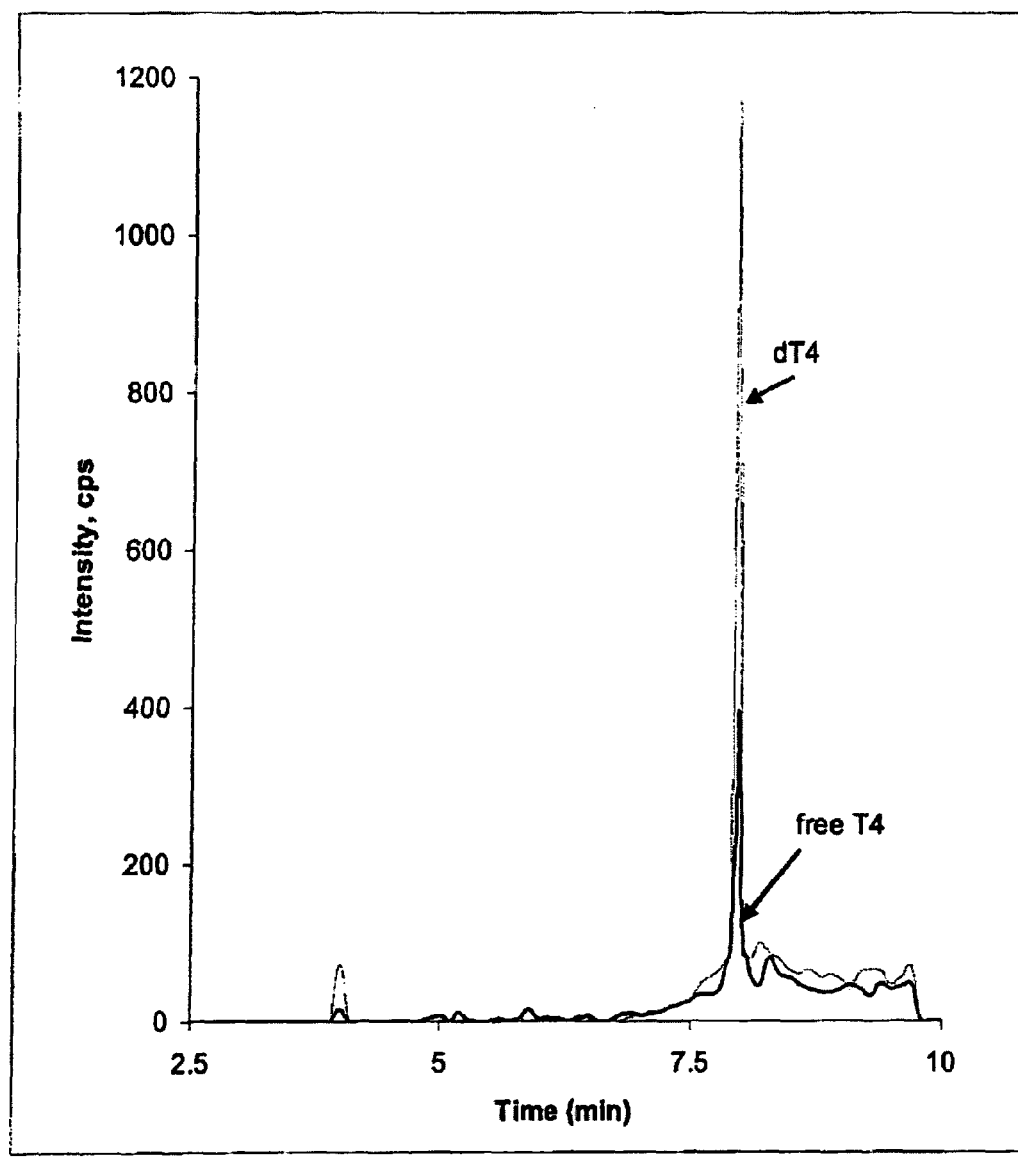
FIG. 6 is a graph showing a typical chromatogram for free T4 (11.2 pg/mL) and deuterated internal standard.

The procedure used is based on an online extraction/cleaning of the injected samples with subsequent introduction into the mass-spectrometer by using a built-in Valco switching valve. 400 μL of the sample was injected onto the Supelco LC-18-DB (3.3 mm×3.0 mm, 3.0 μm ED) chromatographic column equipped with a Supelco Discovery C-18 (3.0 mm) guard column, where it underwent cleaning with 20% (v/v) methanol in 5 mM ammonium acetate pH4.0 at flow rate 0.8 mL/min. After 4 minutes of cleaning the switching valve was activated, the column was flushed with a water/methanol gradient at flow rate of 0.6 mL/min and the samples were introduced into the mass-spectrometer. The gradient parameters that were used are shown in Table 10. The free T4 chromatogram is shown in FIG. 6.

Equilibrium Dialysis

The Nichols free T4 kit (Nichols Institute Diagnostics, Catalogue # 30-0652, San Clemente, Calif.) was used according to the directions provided by the manufacturer. A comparison between the equilibrium dialysis and the tandem mass spectrometric method were performed on patient samples (n=68).

Analogue/Direct Free T4

The Dade RxL Dimension was used for the direct free T4 method. (Dade-Behring Diagnostics, Glasgow, Del.).Results on patient samples were compared with values obtained using tandem mass spectrometry (n=-154).

Between-Day and Within-Day Precision

The between-day and within-day precision was assessed at 3 different concentrations (Table 12).

Results and Discussion

Figure 7:
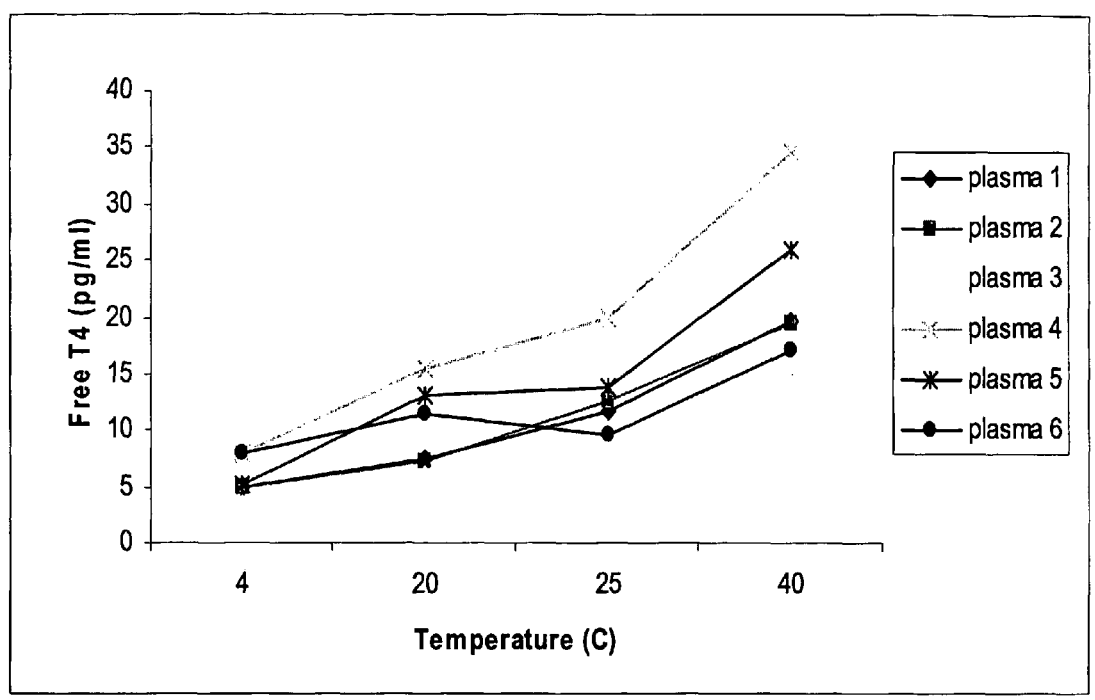
FIG. 7 is a graph showing the effect of temperature on FT4 by tandem mass spectrometry and ultrafiltration.
Figure 8:
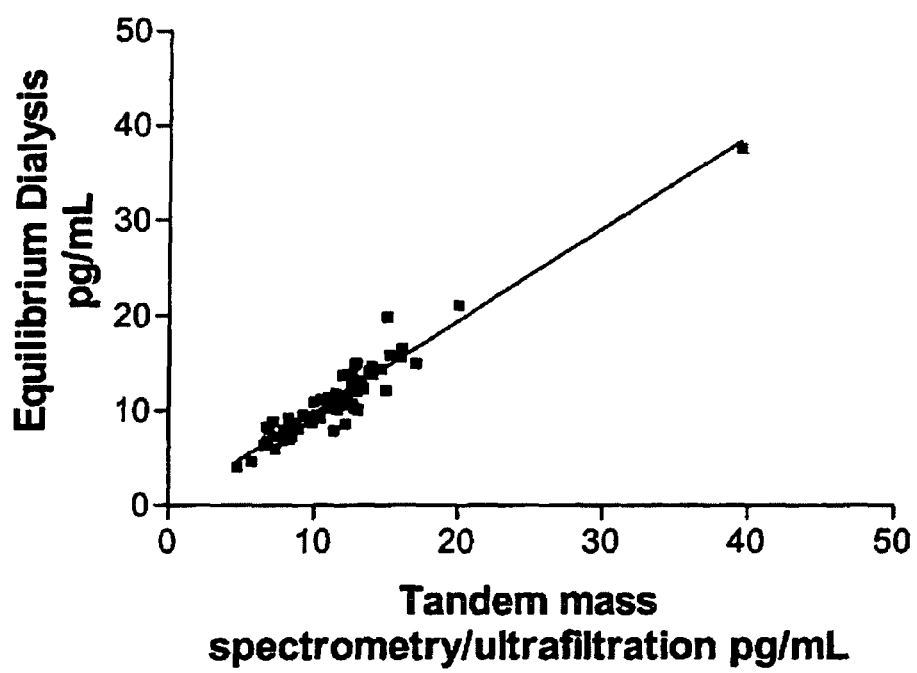
FIG. 8 is graph showing the comparison of the tandem mass spectrometric method with the equilibrium dialysis method for the measurement of free T4.
Figure 9:
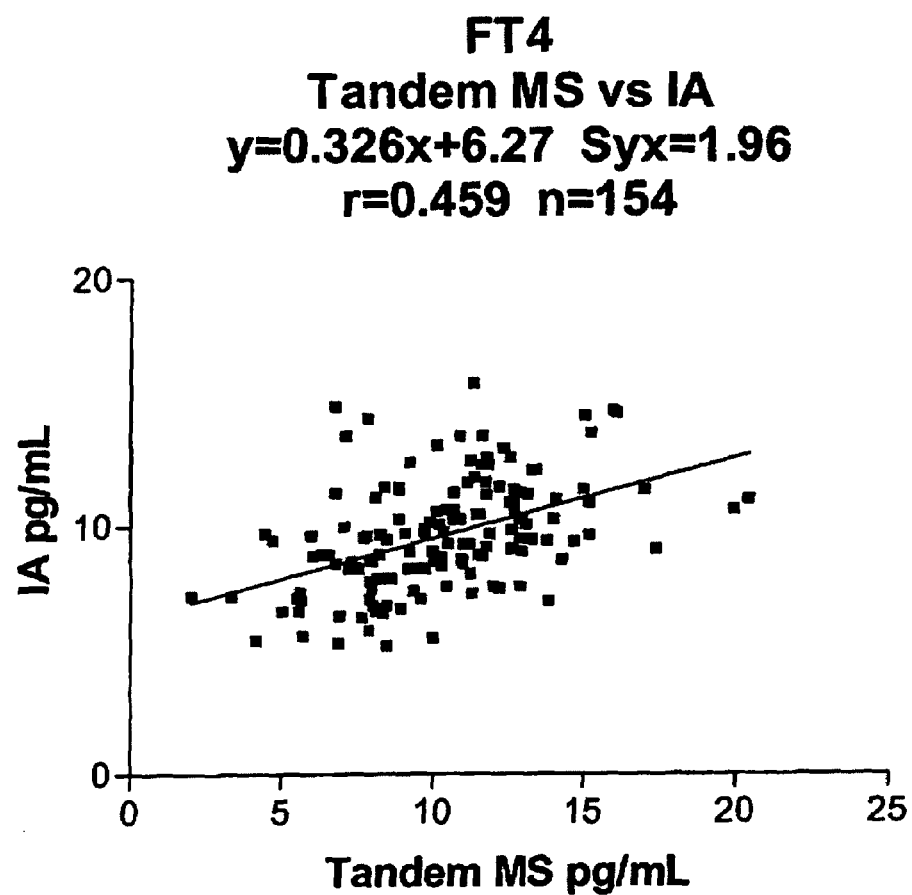
FIG. 9 is a graph showing the comparison of the tandem mass spectrometric method with the direct immunoassay method on the Dade RxL Dimension for the measurement of free T4.

Tables 9 and 10 provide the analytical parameters employed for the tandem mass spectrometric method. FIG. 6 shows a typical chromatogram for free T4 measured by tandem mass spectrometry using the method described. The time per analysis is approximately 8.5 minutes although a steeper gradient could shorten this to about 6 minutes. The Eppendorf centrifuge allows for the centrifugation of 30 tubes simultaneously so that the total run time for 30 patient samples at the 25° C. temperature used is 1 hour plus 3 hours and 15 minutes, or 4 hours and 15 minutes. This ultrafiltration plus LC/MS/MS assay is considerably quicker than the time consuming equilibrium dialysis method. The latter requires 16-18 hour dialysis at 37° C. followed by an immunoassay and therefore the turn-around-time is several days. Also, very few laboratories in North America provide the equilibrium dialysis approach. The concentration of FT4 is temperature dependent (31). If the centrifugation of the Amicon Centrifree tubes occurs at 25° C. (see FIG. 7 and Table 11) the results obtained by the tandem mass spectrometric method closely correlate with those obtained by equilibrium dialysis, which employs a temperature of 37° C. This 12° C. temperature difference is probably the result of different membranes being employed in the equilibrium dialysis and ultrafiltration methods. The correlation between the new isotope dilution tandem mass spectrometric method and the conventional gold standard equilibrium dialysis method was excellent. Equilibrium dialysis=0.971 Mass Spectrometry+0.041, n=68, Syx=1.381, r=0.954 (FIG. 8). In contrast a poor correlation was found with the analogue (direct) FT4 method (Immunoassay=0.326 Mass Spectrometry+6.27, n=154, Syx=1.96, r=0.459, FIG. 9). The between-day and within-day precision shows all concentrations tested gave coefficient of variations (Cvs) of less than 7.1% (Table 12). This performance is superior to that obtained using the difficult equilibrium dialysis method. The lower limit of detection (a reading greater than three standard deviations over the baseline noise) is 2.5 pg/mL.

These studies confirm that the analogue procedures give poor results for free T4 which is further supported when reflex testing for all FT4s below the 2.5[th] percentile and all FT4s above the 97.5[th] percentile which also have normal thyroid-stimulating hormone (TSH) values is done. Approximately 50% of these free T4s run on either the Dade RxL Dimension™ or the DPC Immulite™ give normal results when run by equilibrium dialysis. Finally in the present study, 80% of FT4s greater than the 96.7[th] percentile by tandem MS are associated with TSHs of less than 1.0 uIU/mL (the latter measured by the Dade RxL Dimension™) while in the same cohort of patients, only 40% of FT4s greater than the 96.7[th] percentile measured by direct IA had TSHs of less than 1.0 uIU/mL.

It should also be noted that prior to using tandem mass spectrometry on the plasma ultrafiltrate, attempts were made to measure FT4 on the ultrafiltrate by IA using several approaches which included an RIA kit (Nichols), the Dade RxL™ and DPC IMMULITE™ platforms. In all cases results were exceedingly low indicating that this was not a viable alternative.

In conclusion, a new isotope dilution tandem mass spectrometric method for the measurement of FT4 employing ultrafiltration has been developed. The procedure has excellent precision, compares well with the gold standard. Based on these attractive characteristics this method of FT4 measurement will have a wide applicability in the clinical setting.

TABLE 9

Tandem mass-spectrometer working parameters

| Parameter | Value |
|---|---|
| Curtain gas (CUR) | 14 |
| Gas 1(Nebulizer gas) | 45 |
| Gas2 (Heater gas) | 20 |
| CAD gas | 12 |
| TurboIon Spray (IS) voltage | −4500 V |
| Entrance Potential (EP) | −10 V |
| Collision cell Exit Potential (CXP) | −4 V |
| Source t | 650° |
| Dwell time | 250 msec |

TABLE 10

Gradient parameters

| Time | Methanol (%) |
|---|---|
| 0.0 | 10 |
| 2.5 | 20 |
| 3.5 | 20 |
| 3.6 | 95 |
| 4.5 | 99 |
| 5.9 | 100 |

TABLE 11

Effect of temperature on free T4 and on FT4/TT4 ratios

Free T4 (pg/mL)

| Plasma | LC/MS/MS after ultrafiltration | | | | Equilidrium dialysis | LC/MS/MS after Eq. dial |
|---|---|---|---|---|---|---|
| | 4 C. | 20 C. | 25 C. | 40 C. | | |
| 40598 | 4.88 | 7.54 | 11.80 | 19.63 | 11.57 | 12.45 |
| 06409 | 4.85 | 7.36 | 12.67 | 19.43 | 10.77 | 12.05 |
| 09287 | 3.62 | 6.17 | 8.26 | 14.23 | 6.94 | 8.32 |
| 53230 | 8.06 | 15.53 | 19.97 | 34.57 | 21.11 | 20.80 |
| 46537 | 5.26 | 13.03 | 13.80 | 25.90 | 14.17 | 13.70 |
| 40620 | 7.87 | 11.50 | 9.69 | 17.00 | 9.42 | 10.40 |

*MS Dial - samples running on MS after dialysis

Free T4/Total T4*

| Plasma | LC/MS/MS after ultrafiltration | | | | Equilidrium dialysis | LC/MS/MS after Eq. dial |
|---|---|---|---|---|---|---|
| | 4 C. | 20 C. | 25 C. | 40 C. | | |
| 40598 | 0.067 | 0.104 | 0.163 | 0.271 | 0.160 | 0.172 |
| 06409 | 0.086 | 0.131 | 0.225 | 0.345 | 0.191 | 0.214 |
| 09287 | 0.074 | 0.126 | 0.169 | 0.291 | 0.142 | 0.170 |
| 53230 | 0.166 | 0.319 | 0.410 | 0.710 | 0.433 | 0.427 |
| 46537 | 0.140 | 0.347 | 0.368 | 0.690 | 0.378 | 0.365 |
| 40620 | 0.158 | 0.232 | 0.195 | 0.342 | 0.190 | 0.209 |

*Free T4 (pg/mL), Total T4 (ng/mL)

TABLE 12

Within-day and Between-day precision

| | Within-day (n = 10) | | Between-day (n = 20) | |
|---|---|---|---|---|
| Control | Mean (pg/mL) | CV (%) | Mean (pg/mL) | CV (%) |
| Low | 6.6 | 4.1 | 6.6 | 7.1 |
| Medium | 12.7 | 6.4 | 12.8 | 7.1 |
| High | 26.2 | 6.6 | 24.4 | 6.7 |

This demonstrates a simple method for preparing and detecting FT4 by mass spectrometry.

5. Analysis of Thyroid Hormones and Steroid Hormones

A sample of 500 to 1000 μL of plasma is used. Proteins are precipitated with 150 μL of acetonitrile and vortexed. The sample is centrifuged, and 200 μL of the supernatant is injected onto a C-18 column coupled to a tandem mass spectrometer (LC/MS/MS). The column is washed with 20% methanol in 5 mM ammonium acetate for 3 minutes. The valve on the column is switched and the sample is eluted in a methanol gradient of 20 to 100%. The total run time is 10 minutes. Slight adjustments to the volumes, concentrations and times described can be made, as is known to those skilled in the art.

A sample of the eluant is introduced into an ion-spray ionization chamber and analyzed by API 3000™ mass spectrometer using the negative mode for thyroid hormones in the sample. Steroid hormones in the sample are ionized by photoionization, with the spectrometer in the negative or positive mode. Analysis in the positive mode is typically made for DHEA, Aldosterone, Cortisol, 11-Deoxycortisol, Androstenedione, Testosterone, Estradiol, 17-OH Progesterone, Progesterone, Allopregnalone, Vitamin D, 25,hydroxyl Vitamin D, 1,25 dihydroxy Vitamin D, corticosterone and aldosterone, whereas analysis in the negative mode is typically made for 16-OH Estrone, 2-OH Estrone, Estriol and DHEAS. However, it is possible to analyze any of the hormones in either positive or negative mode.

This demonstrates a simple method of preparing a complex biological matrix for analysis of possible steroid and thyroid hormone content. Steroid hormones which are run in the negative mode can be run simultaneously with the thyroid hormones.

The results indicate that this technique, allows for the identification and characterization of low levels of thyroid hormone in human plasma and saliva.

6. Analysis of FT3 Hormone

FT3 was analyzed by the same method as FT4 (Example 4), except for the analysis of the same transition ions for total T3 and using the API 5000™ mass spectrometer.

7. Simultaneous Analysis of FT4 and FT3

Patients with either hyperthyroidism or hypothyroidism require frequent assessment of thyroid function through measurement of their FT4 and FT3 concentrations. Further, people with thyroid ablation require thyroid replacement therapy, such as synthroid. Measurement of their FT4 and FT3 concentrations is important when assessing their dosage regimen. Accordingly, an efficient assay method for the simultaneous analysis of FT3 and FT4 is beneficial.

Figure 10A:
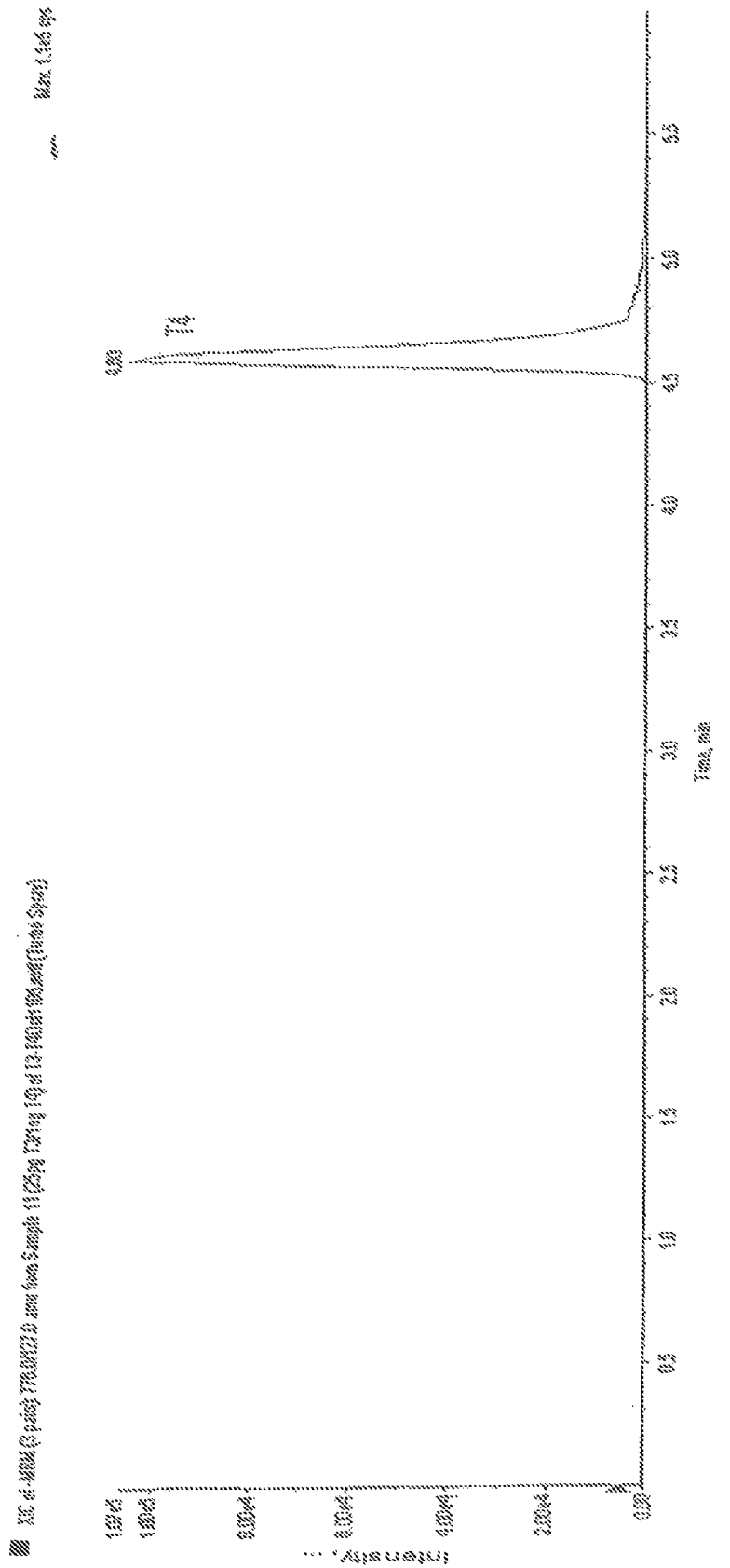
FIGS. 10a, b, and c are a series of mass spectrums showing the analysis of FT4 (a), FT3 (b), and FT4-d2 (c) using an API 5000™.
Figure 10C:
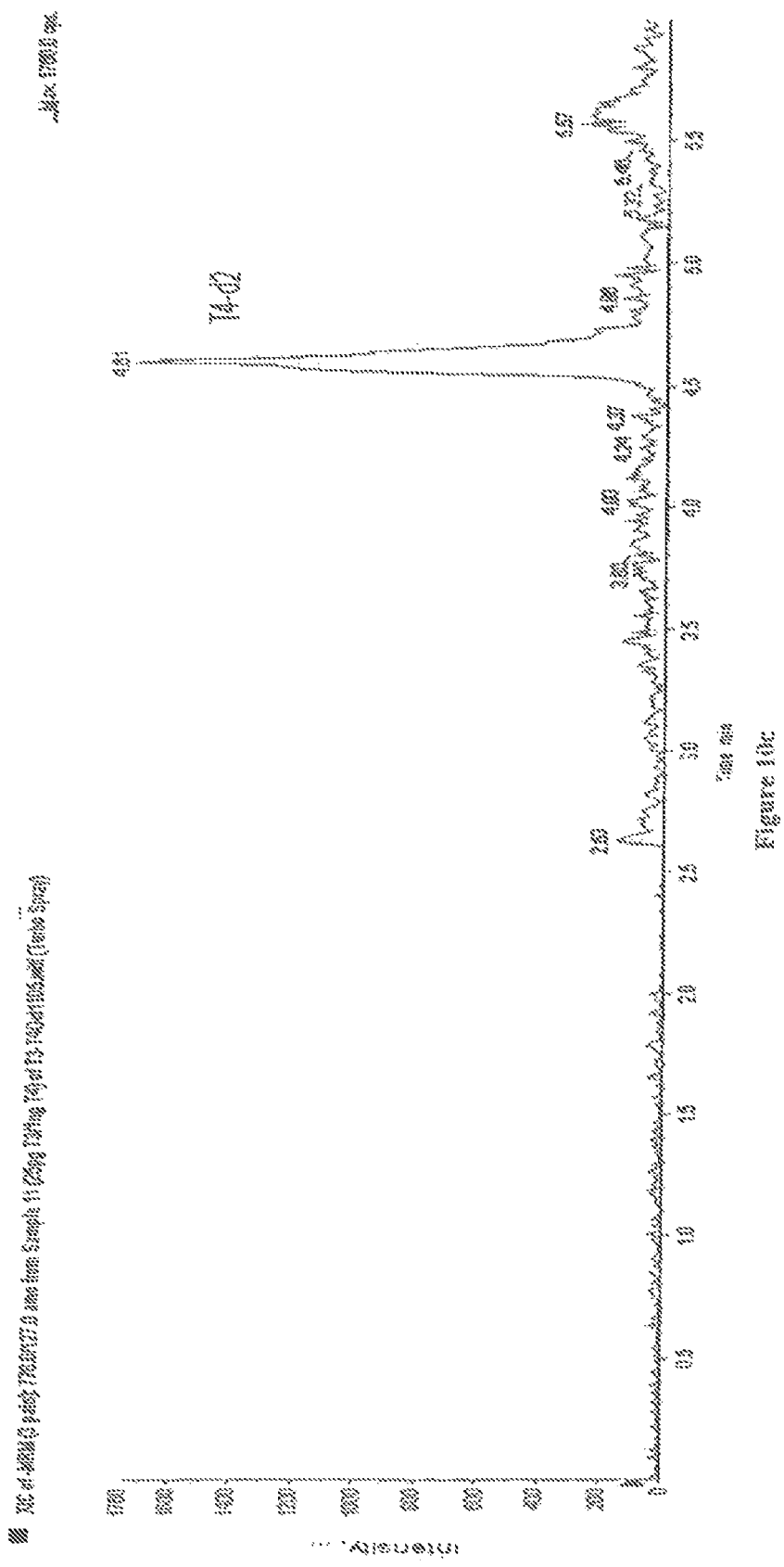

FT4 and FT3 were analyzed simultaneously by a similar method of Example 4 except using the API 5000™ mass spectrometer. 100 μL mixture of T3 (25 pg/mL) and T4 (1 ng/mL) with internal standard T4-d2 were injected onto the column by autosampler, and the column was washed by 20% MeOH buffer for 2 minutes. Gradient elution started from 20% MeOH to 100% MeOH in 2 minutes after the Valco valve was activated at 2 minutes, and then kept at 100% for another 2 minutes. The retention times were: T3, 4.34 minutes, T4, 4.60 minutes, and T4-d2, 4.61 minutes. FIG. 10 shows the mass spectrums of the analytes. Standard curves for FT3 (1-25 pg/ml) and FT4 (5-50 pg/ml) can be run with the analysis of the samples.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

References

All references listed herein are incorporated by reference in their entirety.

1. Lum S M, Nicoloff Y T, Spencer C A, Kaptein E M. Peripheral tissue mechanism for maintenance of serum triiodothyronine values in a thyroxine-deficient state in man. J Clin Invest 1984; 73 (2):570-575.
2. Sakata S, Nakamura S, Miura K. Autoantibodies against thyroid hormones or iodothyronine. Implications in diagnosis, thyroid function, treatment, and pathogenesis. Ann Intern Med 1985; 103 (4):579-589.
3. Beck-Peccoz P, Romelli P B, Cattaneo M G, Faglia G, White E L, Barlow J W, Stockigt J R. Evaluation of free thyroxine methods in the presence of iodothyronine-binding autoantibodies. J Clin Endocrinol Metab 1984; 58(4): 736-739.
4. Klee G G. Human anti-mouse antibodies. Arch Pathol Lab Med 2000; 124(6): 921-923.
5. College of American Pathologists Proficiency Survey Report on Y-03, RAP-03 and K-06 specimens for 2003.
6. Soldin S J. Digoxin—issues and controversies. Clin Chem 1986; 32(1 Pt 1):5-12.
7. Soldin S J, Papanastasiou-Diamandi A, Heyes J, Lingwood C, Olley P. Are immunoassays for digoxin reliable? Clin Biochem 1984; 17(5):317-320.
8. Thong B, Soldin S J, Lingwood C A. Lack of specificity of current anti-digoxin antibodies, and preparation of a new, specific polyclonal antibody that recognizes the carbohydrate moiety of digoxin. Clin Chem 1985; 31(10):1625-1631.
9. Murthy J N, Davis D L, Yatscoff R W, Soldin S J. Tacrolimus metabolite cross-reactivity in different tacrolimus assays. Clin Biochem 1998; 31(8):613-617.
10. Murthy J N, Yatscoff R W, Soldin S J. Cyclosporine metabolite cross-reactivity in different cyclosporine assays. Clin Biochem 1998; 31(3 ):159-163.
11. Shen S, Elin R J, Soldin S J. Characterization of cross reactivity by carbamazepine 10,11-epoxide with carbamazepine assays. Clin Biochem 2001; 4(2):157-158.
12. Ghoshal A K, Soldin S J. tacrolimus II assay: is it reliable at low blood concentrations? A comparison with tandem MS/MS. Clin Biochem 2002; 35(5): 389-392.
13. Soldin S J, Steele B W, Witte D L, Wang E, Elin R J. Lack of specificity of cyclosporine immunoassays. Results of a College of American Pathologists Study. Arch Pathol Lab Med 2003; 127(1):19-22.
14. Despres N, Grant A M. Antibody interference in thyroid assays: a potential for clinical misinformation. Clin Chem 1998; 44(3 ):440-454.
15. Sarne D H, Refetoff S, Nelson J C, Linarelli L G. A new inherited abnormality of thyroxine-binding globulin (TBG-San Diego) with decreased affinity for thyroxine and triiodothyronine. J Clin Endocrinol Metab 1989; 68(1): 114-119.
16. Burman K D, Bongiovanni R, Garis R K, Wartofsky L, Boehm T M. Measurement of serum T4 concentration by high performance liquid chromatography. J Clin Endocrinol Metab, 1981; 53(5): 909-912.
17. Tai S S, Sniegoski L T, Welch M J. Candidate reference method for total thyroxine in human serum: use of isotope-dilution liquid chromatography-mass spectrometry with electrospray ionization. Clin Chem 2002; 48(4):637-642.

18. Thienpont L M, De Brabandere V I, Stockl D, De Leenheer A P. Development of a new method for the determination of thyroxine in serum based on isotope dilution gas chromatography mass spectrometry. Biol Mass Spectrom 1994; 23 (8): 475-482.
19. Thienpont L M, Fierens C, De Leenheer A P, Przywara L. Isotope dilution-gas chromatography/mass spectrometry and liquid chromatography/electrospray ionization-tandem mass spectrometry for the determination of triiodo-L-thyronine in serum. Rapid Commun Mass Spectrom 1999; 13 (19):1924-1931.
20. De Brabandere V I, Hou P, Stockl D, Thienpont L M, De Leenheer A P. Isotope dilution-liquid chromatography/electrospray ionization-tandem mass spectrometry for the determination of serum thyroxine as a potential reference method. Rapid Commun Mass Spectrom 1998; 12(16): 1099-1103.
21. Ramsden, D. B. and M. J. Farmer, Development of a gas chromatographic selected ion monitoring assay for thyroxine (T4) in human serum. Biomed Mass Spectrom 1984; 11(8):421-427.
22. Nishinaga A, Cahnmann H J, Kon H, Matsuura T. Model reactions for the biosynthesis of thyroxine. XII. The nature of a thyroxine precursor formed in the synthesis of thyroxine from diiodotyrosine and its keto acid analog. Biochemistry 1968; 7(1):388-397.
23. Choi M H, Kim, J N, Chung B C. Rapid HPLC-Electrospray Tandem Mass Spectrometric Assay for Urinary Testosterone and Dihydrosterone Glucuronides from Patients with Benign Prostate Hyperplasia. Clin Chem 2003;49(2): 22-325.
24. Biancotto G, Angeletti R, Traldi P, Silvestri M S, Guidugli F. Determination of 17β-Estradiol in Bovine Plasma: Development of a Highly Sensitive Technique by Ion Trap Gas Chromatography-Tandem Mass Spectrometry Using Negative Ion Chemical Ionization. J Mass Spectrom2002; 37: 1226-1271.
25. Lai C C, Tsai C H, Tsai F J, Wu J Y, Lin W D, Lee C C. Rapid Screening Assay of Congenital Adrenal Hyperplasia by Measuring 17αHydroxy-progesterone with High-Performance Liquid Chromatography/Electrospray Ionization Tandem Mass Spectrometry From Dried Blood Spots. J Clin Lab Anal 2002;16: 20-25.
26. Vierhapper H, Nowotny P, Waldausl W. Reduced Production Rates of Testosterone and Dihydrosterone in Healthy Men Treated with Rosiglitazone. Metabolism 2000;52(2): 230-232.
27. Nelson J C, Wilcox R B. Analytical performance of free and total thyroxine assays. Clin Chem 1996; 42(1):146-154.
28. Evans S E, Burr W A, Hogan T C. A reassessment of 8-anilino-l-naphthalene sulphonic acid as a thyroxine binding inhibitor in the radioimmunoassay of thyroxine. Ann Clin Biochem 1977; 14(6):330-334.
29. Ekins R. Validity of Analogue Free Thyroxin Immunoassays. Clin Chem 1987; 33:2137-52.
30. Tai S S, Sniegoski L T, Welch M J. Candidate reference method for total thyroxine in serum: use of isotope-dilution liquid chromatography-mass spectrometry with electrospray ionization. Clin Chem 2002; 48: 637-42.
31. van der Sluijs Veer G., Vermes I, Bonte H A, Hoorn R K J. Temperature effects on Free-Thyroxine Measurements: Analytical and Clinical Consequences. Clin Chem 1992; 38:1327-31.

What is claimed is:
1. A method for mass spectrometric analysis of a sample containing or suspected of containing free thyroxine (FT4) hormone, consisting of:
    (a) providing a sample containing or suspected of containing FT4 hormone;
    (b) separating FT4 hormone from the sample and from bound T4 by liquid chromatography, centrifugation using an ultrafiltration device, equilibrium dialysis or combinations thereof;
    (c) collecting FT4 hormone separated from bound T4; and
    (d) analyzing FT4 hormone separated from bound T4 using a mass spectrometer.
2. The method according to claim 1 wherein the size of said sample containing or suspected of containing FT4 hormone is at least about 500 µL.
3. The method according to claim 1 wherein the step of separating the FT4 hormone from the sample and from bound T4 further comprises an on-line extraction and a built-in switch valve.
4. The method according to claim 1 wherein said step of analyzing the FT4 hormone separated from bound T4 using a mass spectrometer comprises multiple reaction monitoring.
5. The method according to claim 1 wherein said step of analyzing the FT4 hormone separated from bound T4 using a mass spectrometer comprises selected ion monitoring.
6. The method of claim 1 wherein the step of separating FT4 hormone from the sample and from bound T4 comprises use of ultrafiltration device using a mesh size of approximately 30,000 MW.
7. The method of claim 6 wherein the FT4 hormone is separated by centrifugation at about 25° C. for about 1 hour.
8. The method according to claim 1 wherein the sample containing or suspected of containing FT4 hormone is obtained from a biological sample selected from blood, plasma, serum, urine and saliva, or any combination thereof.
9. The method of claim 8 wherein the biological sample is blood.
10. The method of claim 8 wherein the biological sample is plasma.
11. The method of claim 8 wherein the biological sample is serum.
12. The method of claim 8 wherein the biological sample is urine.
13. The method of claim 8 wherein the biological sample is saliva.
14. The method according to claim 1 wherein the mass spectrometer is a liquid chromatography-tandem-mass spectrometer.
15. The method according to claim 14 wherein the liquid chromatography-tandem mass spectrometer is equipped with an electrospray ionization source.
16. The method according to claim 1 wherein said step of analyzing the FT4 hormone separated from bound T4 using a mass spectrometer comprises an ionization technique selected from photoioinization, electrospray ionization, atmospheric pressure chemical ionization, and electron capture ionization.
17. The method according to claim 16 wherein said ionization technique is electrospray ionization.
18. The method according to claim 17 wherein said ionization is performed in negative mode.
19. The method of any one of claims 1, 6 or 7 and 5 wherein the mass spectrometer is a triple quadrupole.
20. A method for mass spectrometric analysis of a sample containing or suspected of containing free thyroxine (FT4) hormone, consisting of:

(a) providing a sample containing or suspected of containing FT4 hormone;
(b) separating FT4 hormone from the sample and from bound T4 using an ultrafiltration device with a mesh size of approximately 30,000 MW;
(c) collecting FT4 hormone separated from bound T4; and
(d) analyzing FT4 hormone separated from bound T4 using a mass spectrometer.

21. The method of claim 20 wherein the FT4 hormone is separated by centrifugation at about 25° C. for about 1 hour.

22. The method according to claim 20 wherein the sample containing or suspected of containing FT4 hormone is obtained from a biological sample selected from blood, plasma, serum, urine and saliva, or any combination thereof.

23. The method according to claim 20 wherein the size of said sample containing or suspected of containing FT4 hormone is at least about 500 μL.

24. The method according to claim 20 wherein the step of separating the FT4 hormone from the sample and from bound T4 further comprises an on-line extraction and a built-in switch valve.

25. The method according to claim 20 wherein said step of analyzing the FT4 hormone separated from bound T4 using a mass spectrometer comprises multiple reaction monitoring.

26. The method according to claim 20 wherein said step of analyzing the FT4 hormone separated from bound T4 using a mass spectrometer comprises selected ion monitoring.

27. The method according to claim 20 wherein the mass spectrometer is a triple quadrupole.

28. The method according to claim 20 wherein the mass spectrometer is a liquid chromatography-tandem-mass spectrometer.

29. The method according to claim 28 wherein the liquid chromatography-tandem mass spectrometer is equipped with an electrospray ionization source.

30. The method according to claim 20 wherein said step of analyzing the FT4 hormone separated from bound T4 using a mass spectrometer comprises an ionization technique selected from photoioinization, electrospray ionization, atmospheric pressure chemical ionization, and electron capture ionization.

31. The method according to claim 30 wherein said ionization technique is electrospray ionization.

32. The method according to claim 31 wherein said ionization is performed in negative mode.

* * * * *